United States Patent
Lee et al.

(10) Patent No.: US 10,696,753 B2
(45) Date of Patent: Jun. 30, 2020

(54) METHOD OF ELECTROCHEMICALLY MODIFYING SURFACE OF ELECTRODE USING DOPAMINE-HYALURONIC ACID CONJUGATES

(71) Applicant: Gwangju Institute of Science and Technology, Gwangju (KR)

(72) Inventors: Jae Young Lee, Gwangju (KR); Semin Kim, Jeonju-si (KR); Yesul Jang, Gwangju (KR)

(73) Assignee: GWANGJU INSTITUTE OF SCIENCE AND TECHNOLOGY, Gwangju (KR)

( * ) Notice: Subject to any disclaimer, the term of this patent is extended or adjusted under 35 U.S.C. 154(b) by 210 days.

(21) Appl. No.: 15/783,553

(22) Filed: Oct. 13, 2017

(65) Prior Publication Data
US 2018/0105611 A1     Apr. 19, 2018

(30) Foreign Application Priority Data
Oct. 14, 2016   (KR) .................. 10-2016-0133487

(51) Int. Cl.
  *C07C 215/28*     (2006.01)
  *C08B 37/08*      (2006.01)
  (Continued)

(52) U.S. Cl.
  CPC ........ *C08B 37/0072* (2013.01); *C07C 215/28* (2013.01); *G01N 27/30* (2013.01); *G01N 23/2273* (2013.01)

(58) Field of Classification Search
  CPC ....................................................... C25D 9/02
  See application file for complete search history.

(56) References Cited

U.S. PATENT DOCUMENTS

2007/0281148 A1*  12/2007  Bureau ................ C09D 5/4476
                                                      428/336

FOREIGN PATENT DOCUMENTS

KR    102012-0129211    * 11/2012   ............... B05D 1/18

OTHER PUBLICATIONS

Wu et al, "Multifunctional Coating Based on Hyaluronic Acid and Dopamine Conjugate for Potential Application on Surface Modification of Cardiovascular Implanted Devices," ACS Appl. Mater. Interfaces, 2015 (Year: 2015).*

(Continued)

*Primary Examiner* — Salil Jain
(74) *Attorney, Agent, or Firm* — Hauptman Ham, LLP

(57) ABSTRACT

Provided are a method of electrically modifying an electrode surface with dopamine-hyaluronic acid conjugates and technologies to suppress adsorption of harmful biomaterials and organisms by imparting anti-fouling to the electrode surface using the same and to maintain electrical properties of the electrode. More specifically, provided is a technology of coating an electrode surface via a dopamine functional group by electrochemically oxidizing dopamine-conjugated biocompatible polysaccharide polymers around the electrode. This aims to confirm the capability of suppressing organism adhesion depending on whether or not cells are adsorbed after coating the electrode surface, and to identify that electrochemical performance of the electrode is maintained or a slight increase in electrode resistance is kept, even after the electrode coating. The surface modified electrode according to the present invention can be widely used in the field of biomaterials such as bio-electrodes, biosensors and cell supports.

5 Claims, 7 Drawing Sheets

(51) Int. Cl.
*G01N 27/30* (2006.01)
*G01N 23/2273* (2018.01)

(56) References Cited

OTHER PUBLICATIONS

Huang et al.; "Conjugation of Hyaluronic Acid onto Surfaces via the Interfacial Polymerization of Dopamine to Prevent Protein Adsorption", Langmuir; Publication Date (Web): Oct. 21, 2015; pp. 1-32.
Wu et al.; "Multifunctional Coating Based on Hyaluronic Acid and Dopamine Conjugate for Potential Application on Surface Modification of Cardiovascular Implanted Devices"; ACS Applied Materials & Interfaces' Jan. 13, 2016; pp. A-M.

* cited by examiner

Confirmation of selective coating

METHOD OF ELECTROCHEMICALLY MODIFYING SURFACE OF ELECTRODE USING DOPAMINE-HYALURONIC ACID CONJUGATES

CROSS-REFERENCE TO RELATED APPLICATIONS

This application claims priority under 35 U.S.C. § 119 to Korean Patent Application No. 10-2016-0133487 filed on Oct. 14, 2016 in the Korean Intellectual Property Office, the disclosure of which is incorporated herein by reference in its entirety.

BACKGROUND OF THE INVENTION

Field of the Invention

The present invention relates to a method of electrically modifying an electrode surface with dopamine-hyaluronic acid conjugates.

Description of the Related Art

Electrodes used in the field of biology are generally used to give an electrical stimulus to a bio-system or receive an electrical signal therefrom. It is known that, when an electrode material of a bio-electrode contacts a bio system and a biomaterial, non-specific interaction therebetween occurs, thus causing a problem of deteriorated electrical properties. In particular, proteins are non-specifically adsorbed on the electrode surface and the adsorbed proteins are then denatured on the electrode surface, which may induce malfunction of bio-systems, or then promote adsorption of various cells. This is known to lead to problems of increasing electrical resistance of bio-electrodes and deteriorating electrical signal exchange.

In an attempt to suppress such a series of damage to electrode performance and to solve foreign body reaction, there has been suggested a method for minimizing adsorption and denaturation of proteins by modifying the surface of an electrode with a hydrophilic polymer. However, in the case of coating the electrode surface, there is disadvantageously loss of electrical properties of the electrode such as increased resistance of the electrode and coating non-uniformity.

In general, methods for modifying properties of electrodes by adhering biocompatible polymers to the surfaces of the electrodes include physical coating, chemical methods and electrochemical methods. The physical coating includes dissolving a polymer solution in a solvent, coating and then removing the solvent. The chemical method includes chemically reacting a material such as a polymer with the electrode surface and coating the electrode surface. In this case, remaining chemical materials may result in problems including the risk of inducing toxicity and difficulties in controlling reactions and coating, and occurrence of addition reactions, when used as a bio-electrode. In addition, in this case, disadvantageously, it is difficult to selectively coat only the electrode, coating may be formed over the overall part rather than the electrode surface, and it is impossible to control the thickness of coating in detail. In addition, physical and chemical coating methods may bring about problems of an increase in electrode resistance, loss of electrical properties and difficulties in control. The electrochemical method involves reaction occurring only on the electrode surface, unlike chemical methods, thus being advantageous in that surface modification is possible only at a desired position of the electrode, and the surface thickness and properties can be adjusted by controlling a voltage or charge amount, or charge supply time. In particular, coating with polymers by an electrochemical method may include adhering, to a biocompatible polymer, a material that can be adhered to an electrode by an electrochemical method, dissolving the material in a solution, and coating the electrode with the material by applying an oxidation/reduction potential thereto.

Hyaluronic acid is an anionic polysaccharide polymer present in a bio-system, which is used as an ingredient for a variety of biomaterials owing to excellent hydrophilicity and biocompatibility. Conventional methods of electrochemically coating an electrode surface with hyaluronic acid include adhering, to hyaluronic acid, a pyrrole monomer which can be electrochemically oxidized and adhered, to electrochemically coat the electrode surface with the polymer. This method has problems of biocompatibility and the possibility of coating detachment due to low attraction between the pyrrole functional group and electrode surface, since the pyrrole monomer is not a biomaterial.

In addition, there was suggested an electrochemical coating method which includes, regarding a conjugate in which dopamine is bound to polyethylene glycol, producing a polymer, a dopamine functional group of which is converted into a quinone functional group using a chemical oxidizing agent, and applying a reduction potential thereto. This method may cause problems of biocompatibility due to remaining chemicals derived from incorporation of the oxidizing agent to produce quinine, and of non-decomposition of polyethylene glycol polymer upon use for a long time and antibody formation. In addition, the method includes two steps of a chemical method and a chemical coating method and in particular, has a drawback of requiring a long reaction time for electrochemical coating.

PRIOR ART DOCUMENT

Non-Patent Document

1. HUANG et al.; "Conjugation of Hyaluronic Acid onto Surfaces via the Interfacial Polymerization of Dopamine to Prevent Protein Adsorption"; Langmuir; Publication Date (Web): Oct. 21, 2015; pages 1-32
2. W U et al.; "Multifunctional Coating Based on Hyaluronic Acid and Dopamine Conjugate for Potential Application on Surface Modification of Cardiovascular Implanted Devices"; ACS Applied Materials & Interfaces' Jan. 13, 2016; pages A-M

SUMMARY OF THE INVENTION

The problems associated with conventional methods of coating hyaluronic acid are that, due to basic use of a chemical method, coating is formed over the part rather than the electrode surface and it is impossible to precisely control the thickness of coating, and there is a possibility of toxicity induction by residues and side reactions derived from chemicals used.

The present research provides a method of electrochemically modifying an electrode surface that includes synthesizing dopamine-hyaluronic acid conjugates, which exhibit excellent biocompatibility, can be electrochemically adhered and exhibit superior adhesivity to electrodes, and coating only electrodes with the dopamine-hyaluronic acid conjugates by an electrochemical method in a simple manner, to minimize deterioration in electrical and electrochemical properties of the modified electrodes, and to minimize abnormal reaction with biomaterials and deformation owing to hydrophilicity and superior biocompatibility.

Therefore, the present invention has been made in view of the above problems, and it is an object of the present invention to acquire anti-fouling electrodes by synthesizing dopamine-hyaluronic acid conjugates and electrochemically coating electrodes with the same, suppress adsorption of proteins and cells, and at the same time, maintain electrical and electrochemical performance of the modified electrodes.

In accordance with the present invention, the above and other objects can be accomplished by the provision of a method of electrochemically modifying an electrode surface including applying a current to an electrode immersed in a dopamine-hyaluronic acid conjugate solution represented by Formula 1.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE INVENTION

Hereinafter, several aspects and various embodiments of the present invention will be described in more detail.

In accordance with an aspect of the present invention, provided is a method of electrochemically modifying an electrode surface including applying a current to an electrode immersed in a dopamine-hyaluronic acid conjugate solution represented by the following Formula 1:

[Formula 1]

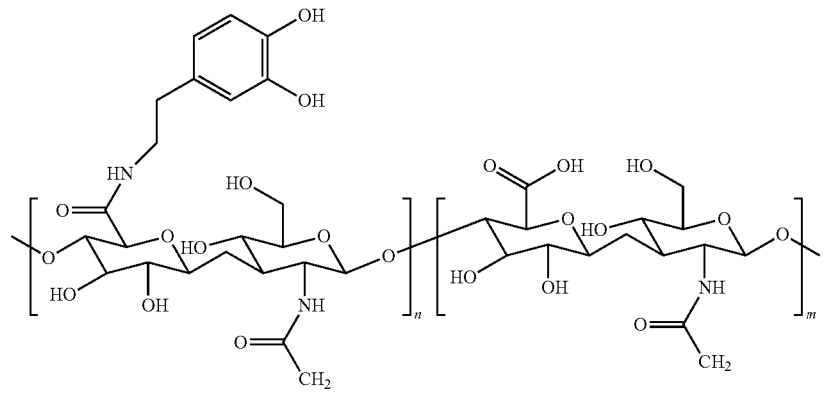

wherein the conjugate has a molecular weight of 35 kDa to 3 MDa and $m/(m+n)$ is 0.03 to 0.3.

Rather than the solution of conjugate of dopamine and hyaluronic acid, a solution of a mixture of dopamine or hyaluronic acid or a polydopamine homopolymer or a polyhyaluronic acid homopolymer may be used, but the effect of surface modification of an electrode is significantly deteriorated, as compared to the method according to the present invention. In addition, in terms of the manufacturing method, like the present invention, the chemical method can be selected in place of electrochemical deposition, but this also causes significant deterioration in surface modification effect.

For example, in cases where a basic atmosphere is formed by mixing dopamine with hyaluronic acid, when dopamine is self-polymerized, hyaluronic acid is incorporated into the polymer. In this case, as polydopamine is depolymerised, hyaluronic acid is slowly dissolved, surface modification effect is remarkably deteriorated reduced, and in particular, the deterioration in effect becomes serious over time.

The conjugate represented by Formula 1 can be prepared as shown in the following Reaction Scheme.

[Reaction Scheme 1]

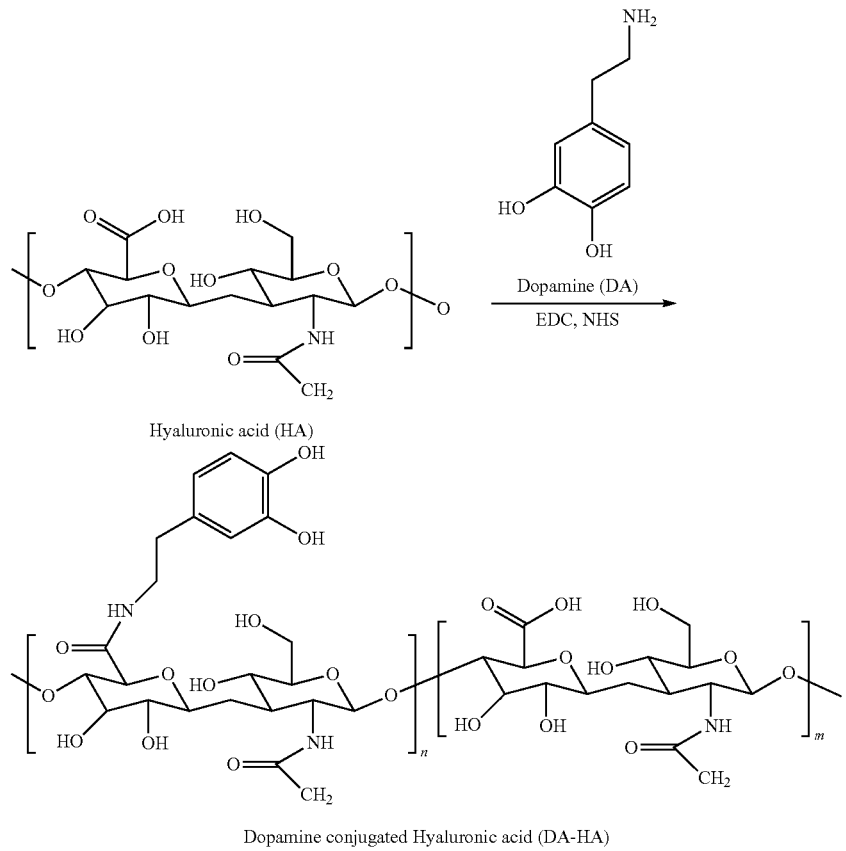

In accordance with an embodiment, regarding the method of electrochemically modifying an electrode surface, a reference electrode and a counter electrode are further immersed in the solution to form a three-electrode cell and a potentiostatic method is used. On the other hand, it is not preferable to use a two-electrode cell type or a galvanostatic method, since the difference in surface modification effect depending on electrode material or surface roughness may occur.

Figure 1A:
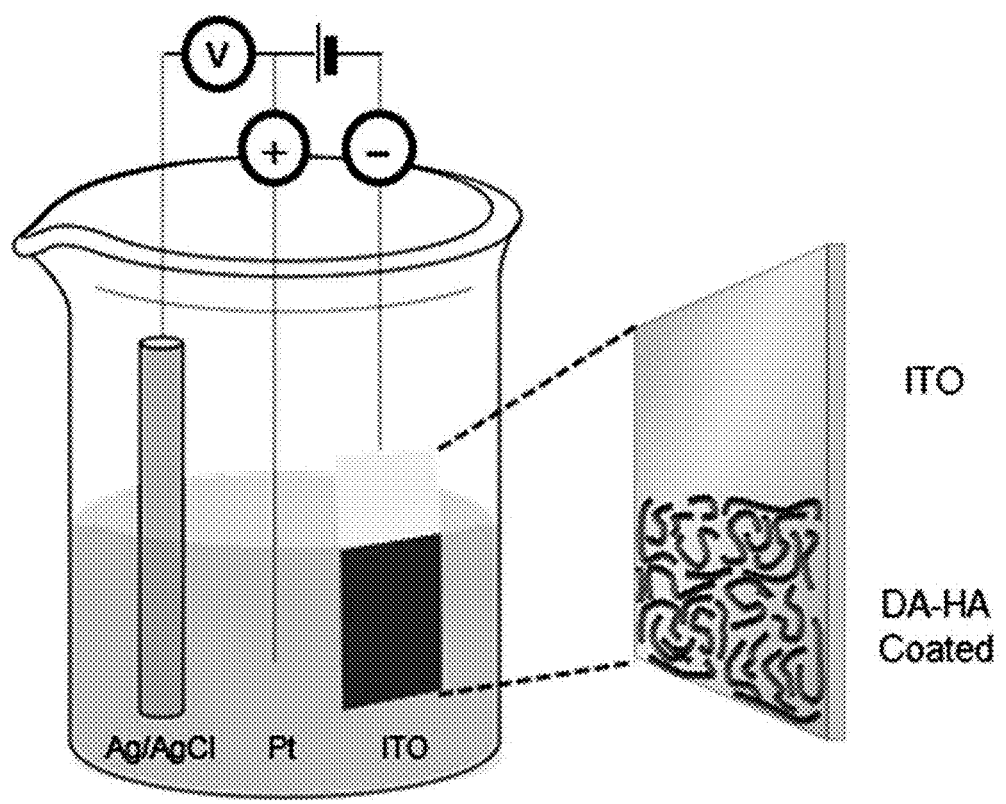
FIG. 1A is an image showing a reaction process by application of a voltage after producing a three electrode cell using dopamine-hyaluronic acid conjugates.

In accordance with another embodiment, the electrode is an ITO electrode or a gold electrode, the reference electrode is a silver/silver chloride reference electrode, and the counter electrode is a Pt electrode. That is, the present invention may be implemented using the three-electrode cell including the working electrode (gold or ITO), the counter electrode (Pt), and the reference electrode as shown in FIG. 1A.

In accordance with another embodiment, the solution has (i) a concentration of the dopamine-hyaluronic acid conjugates of 1 to 10 mg/mL, and (ii) a pH of 2 to 7. In addition, (iii) the current is applied at a constant potential within the range of 0.6 to 1.6 V and (iv) for 50 seconds or longer. In particular, it was confirmed that, unless all of the aforementioned four conditions are satisfied, selective surface modification in a certain area of the electrode may be disadvantageously difficult or impossible. That is, when all four conditions are satisfied, selective surface modification in a certain area of the electrode is possible regardless of the electrode material or surface structure or conditions, but when at least one thereof is not satisfied, such selective surface modification may be impossible.

Hereinafter, the present invention will be described in more detail with reference to the Example and so on, and the scope and contents of the present invention should not be construed as being reduced or limited to the following Example and so on. In addition, it is obvious that the present invention, test results of which are not suggested in detail can be easily implemented by those skilled in the art, based on the disclosure of the present invention including the following Example, and that such modifications and alterations fall within the scope of the claims attached thereto.

In addition, the following test results are only representative test results of Example and Comparative Example and various embodiments of the present invention not suggested exclusively will be described in the corresponding parts in more detail.

Example

Method of Modifying Electrode Surface with Dopamine-Hyaluronic Acid Conjugates by Electrochemical Method An electrode surface was modified with dopamine-hyaluronic acid conjugates using a three-electrode cell.

A dopamine-hyaluronic acid conjugate solution was dissolved in PBS (pH 5) such that the concentration was 3-5 mg/ml. A silver/silver chloride reference electrode was used as the reference electrode, a Pt electrode was used as the counter electrode, and an ITO or gold electrode was used as the working electrode. An electrode was immersed in the prepared solution, and 1.5V was applied for 300 seconds to coat the electrode with the dopamine-hyaluronic acid conjugates. After coating, the electrode was washed with triple distilled water.

Figure 1B:
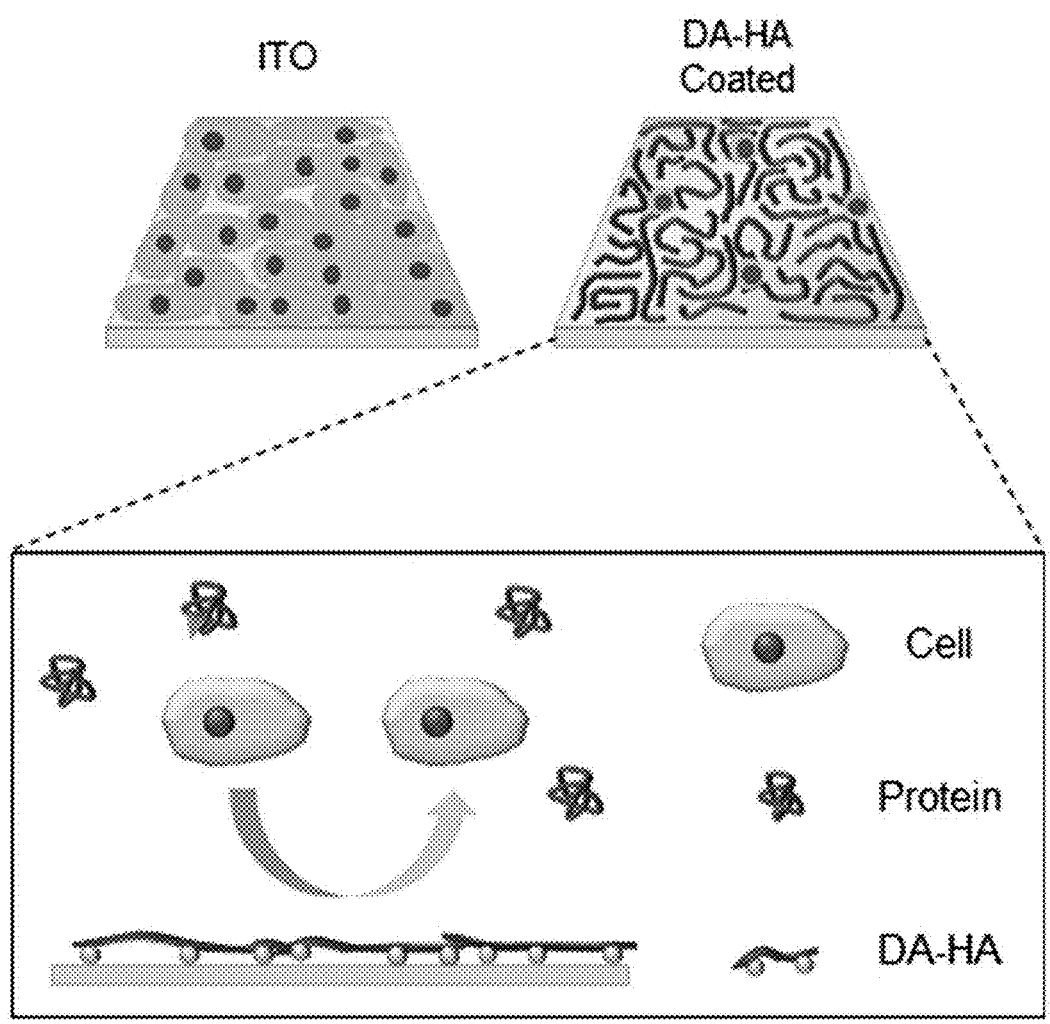
FIG. 1B is a schematic view illustrating that coating with dopamine-hyaluronic acid conjugates can prevent protein adsorption, while cells are adsorbed on a general electrode by abnormal protein adsorption.

As can be seen from FIG. 1B, since the surface of a general electrode (ITO, Au or the like) is hydrophobic, proteins are abnormally adsorbed on the surface thereof, creating injury tissues, but a biocompatible electrode to minimize non-specific protein adsorption and cell adherence can be produced by electrochemically coating with the dopamine-hyaluronic acid conjugate.

Figure 2:
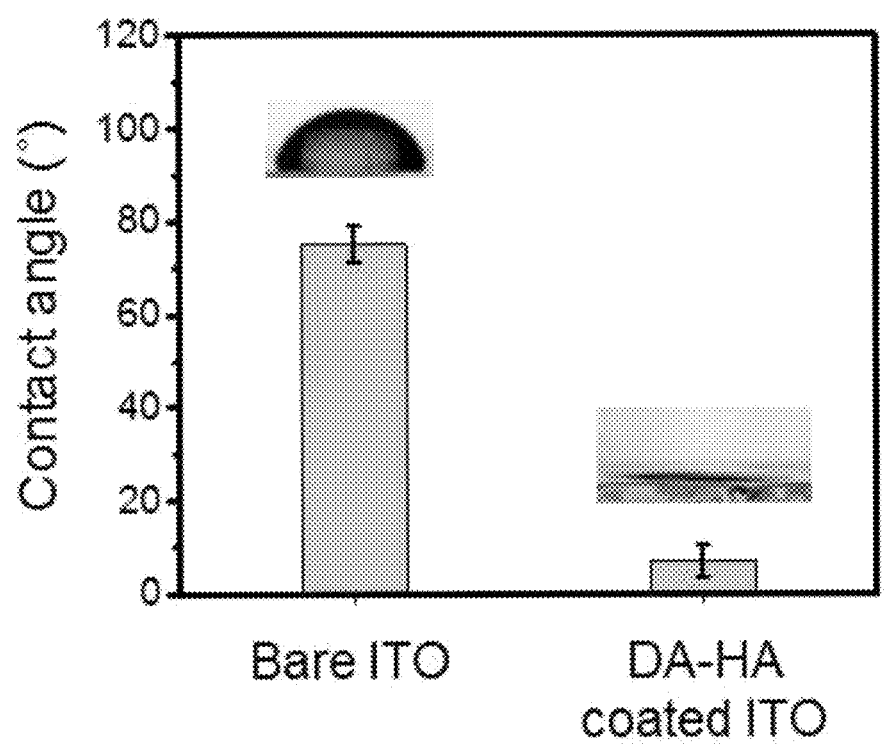
FIG. 2 shows analysis results of X-ray photoelectron spectroscopy (XPS) showing that electrochemically coating with dopamine-hyaluronic acid conjugates can be seen from formation of nitrogen peaks that are not present in the case of an ITO electrode.

As can be seen from FIG. 2, the surface of a general electrode (ITO, Au or the like) has a water contact angle of 60 to 80 degrees and is thus hydrophobic, while the electrode coated with DA-HA has a water contact angle reduced to 3 to degrees and thus has hydrophilicity, like the general electrode.

Figure 3A:
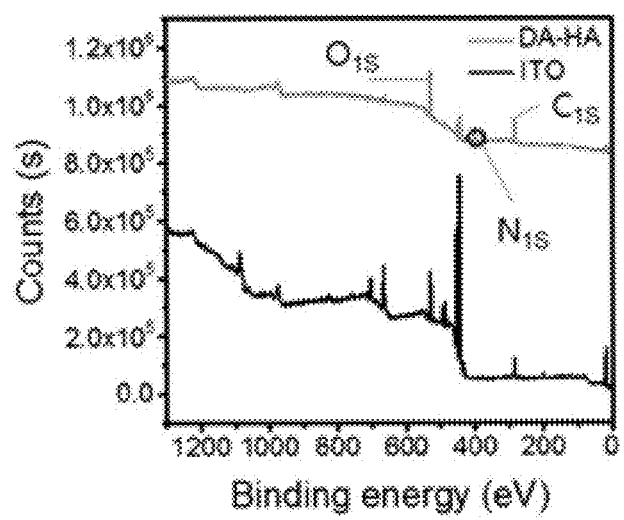
FIG. 3A and FIG. 3B show that, when preparing a solution using an ITO electrode of QCM, the weight of the electrode increases as reaction time increases depending on application of an oxidation/reduction potential, which means that the electrode surface is electrochemically coated with dopamine-hyaluronic acid conjugates to control reaction degree.
Figure 3B:
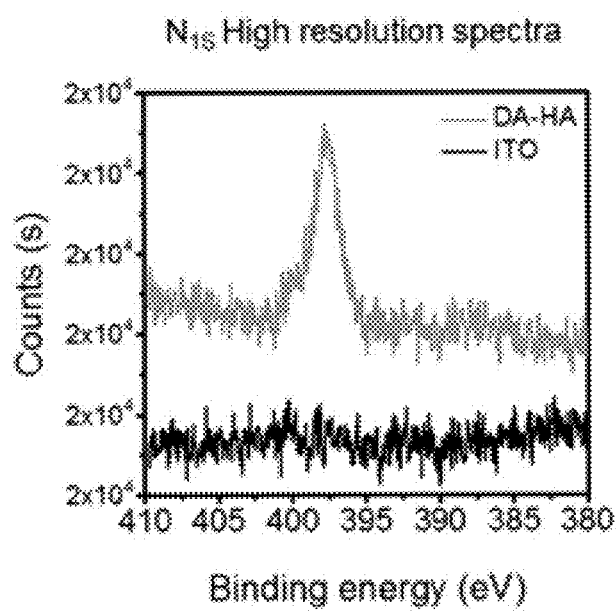

As can be seen from FIG. 3, when the electrode is coated with dopamine-hyaluronic acid conjugates by X-ray photoelectron spectroscopy (XPS), nitrogen atom peak present in hyaluronic acid and dopamine, that is, N1s peak, is generated, which means that electrochemical coating with dopamine-hyaluronic acid conjugates is successful.

Figure 4:
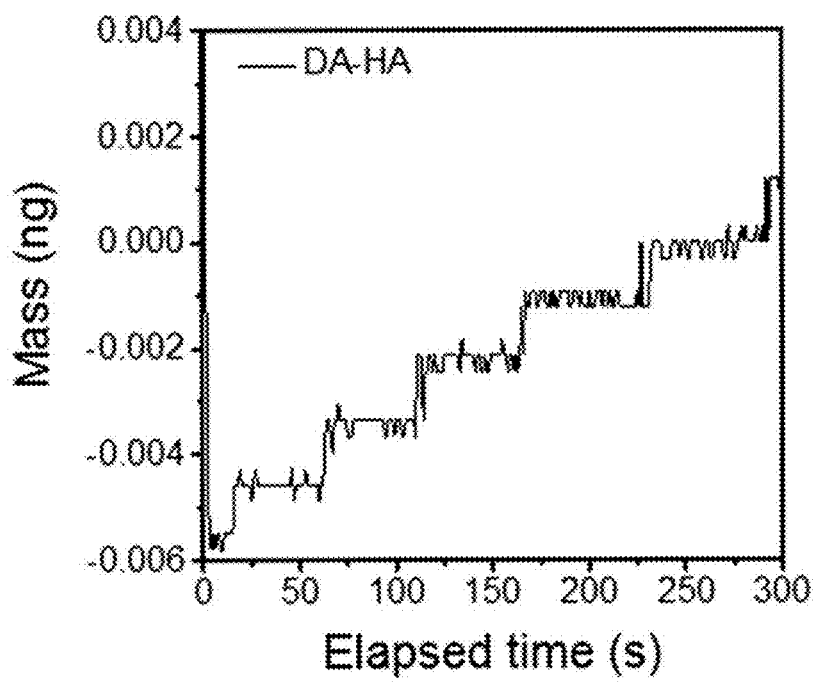
FIG. 4 shows impedance measurement results showing that the impedance of the modified electrode is maintained even after coating with dopamine-hyaluronic acid conjugates.

As can be seen from FIG. 4, a gradual increase in weight is observed by quartz crystal microbalance (QCM), as formation of coating on the electrode surface increases over oxidative reaction time.

Figure 5:
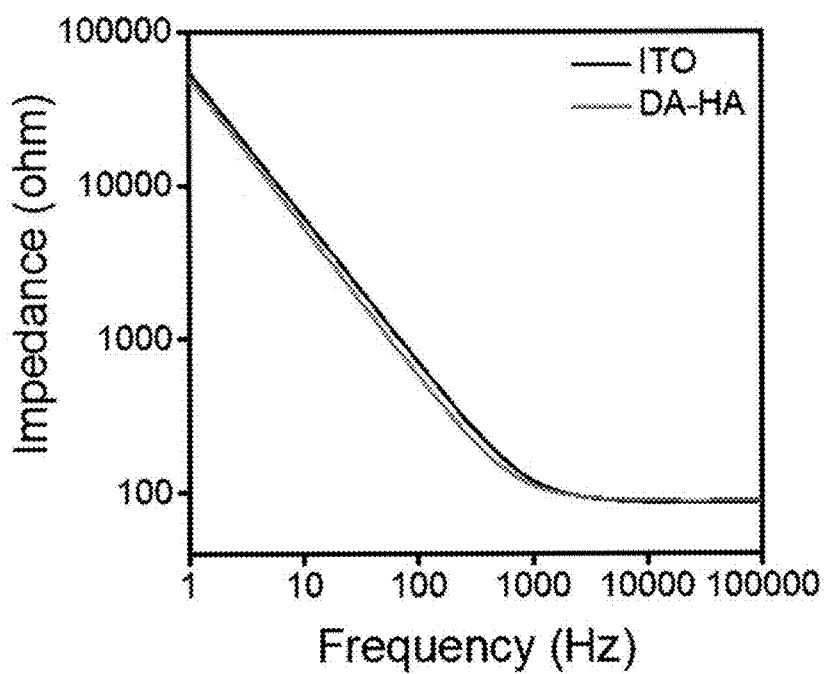
FIG. 5 shows that electrically coating with hyaluronic acid can be confirmed from acid-conjugated proteins labelled with a fluorescent dye and selective coating is possible.

FIG. 5 is a graph showing impedance of the electrode before and after surface modification. Impedance of the electrode is substantially similar to that of an ITO electrode, which indicates that performance of the electrode is maintained even after surface-modification. Accordingly, the electrochemical modification method of the electrode surface with dopamine-hyaluronic acid suggested by the present invention does not cause deterioration in electrical and electrochemical properties of conventional electrodes.

Figure 6:
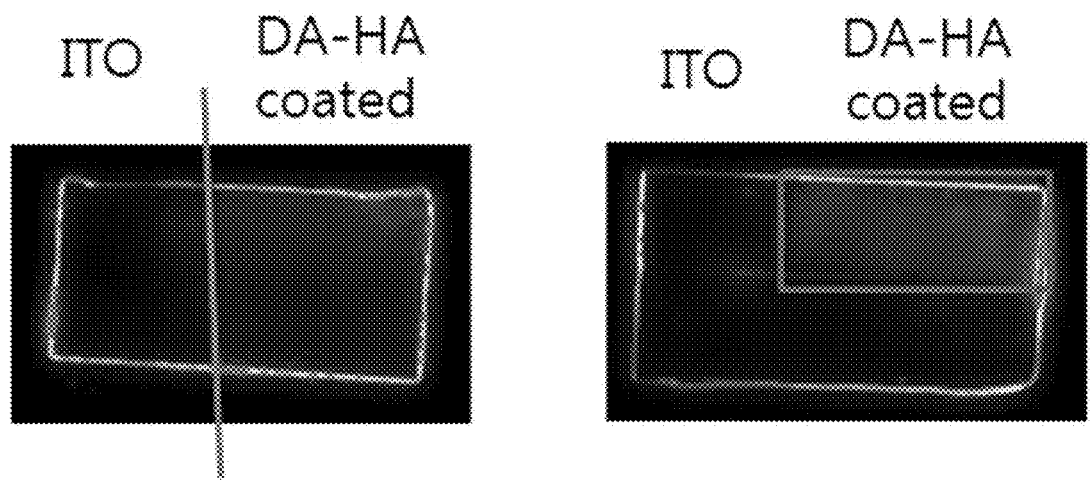
FIG. 6 shows that cells are not adhered to a part coated with dopamine-hyaluronic acid conjugates when fibroblasts are seeded on the electrode.

FIG. 6 shows results of staining using hyaluronic acid-conjugated proteins labelled with a fluorescent dye after coating with dopamine-hyaluronic acid conjugates by an electrochemical method. With this staining method, it is possible to check whether or not the electrode surface is coated with dopamine-hyaluronic acid conjugates because parts where hyaluronic acid is adhered are selectively fluorescent. By identifying the fact that a region where oxidative potential is not applied does not exhibit fluorescence, with this method, only the electrode can be selectively coated with dopamine-hyaluronic acid conjugates based on an electrochemical method.

Figure 7A:
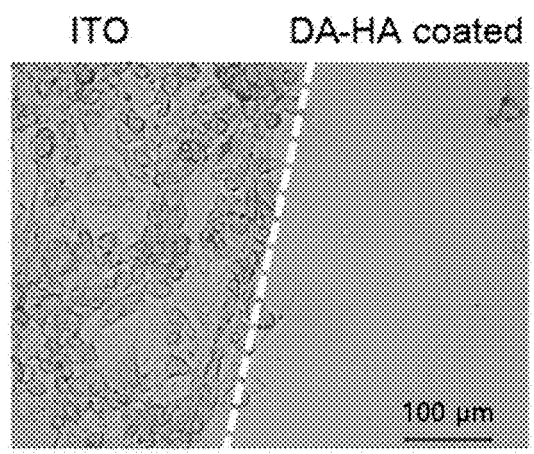
FIG. 7A shows surfaces of the non-modified electrode and the electrode coated with dopamine-hyaluronic acid conjugates.
Figure 7B:
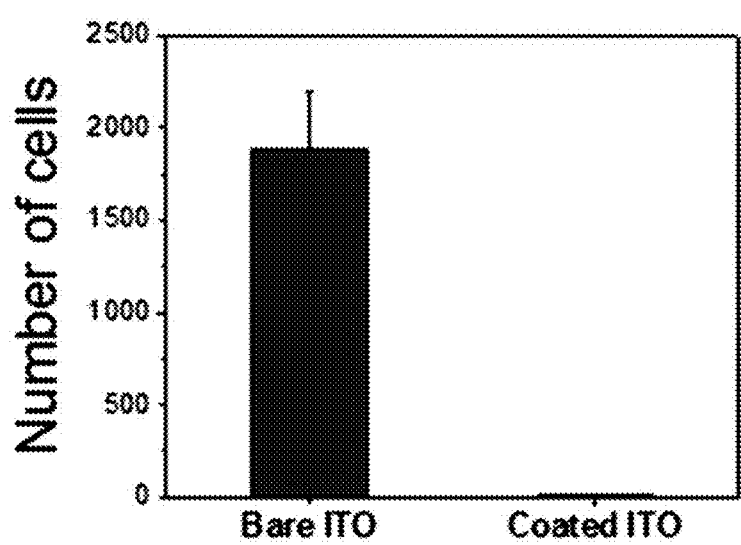
FIG. 7B is a graph indicating numbers of cells in the surfaces of the non-modified electrode and the electrode coated with dopamine-hyaluronic acid conjugates.

As can be seen from FIG. 7, cell adhesivity was checked by observing cells on the electrode. A great amount of cells is adhered to and grown on the non-modified electrode surface before coating of dopamine-hyaluronic acid conjugates, while the electrode coated with dopamine-hyaluronic acid conjugates exhibits similar properties to an anti-fouling electrode to which cells are not adhered.

Coating with dopamine-hyaluronic acid conjugates using an electrochemical method enables selective coating of the electrode, does not affect the performance of the electrode, and allows for production of anti-fouling biocompatible electrodes which are useful as a variety of bio-electrodes.

According to the present invention, only the electrode can be electrochemically coated with dopamine-hyaluronic acid conjugates and, at the same time, conventional problems of non-specific protein adsorption and cell adhesion can be prevented and electrical performance can be maintained. The coating thickness can be adjusted by controlling a voltage and time using an electrochemical method. In addition, by using dopamine, excellent adhesion between the coating material and the electrode can be obtained and superior biocompatibility based on hyaluronic acid can be secured.

The method according to the present invention is advantageous in that, by coating the electrode with a material with hydrophilicity and superior biocompatibility, only necessary parts of the electrode can be selectively coated with dopamine-hyaluronic acid conjugates by an electrochemical method, the thickness of coating can be precisely adjusted by controlling voltage and time, and abnormal bio-reactions can be minimized and thus excellent electrical properties can be obtained.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A method of electrochemically modifying an electrode surface comprising applying a current to an electrode immersed in a solution comprising a compound represented by the following Formula 1:

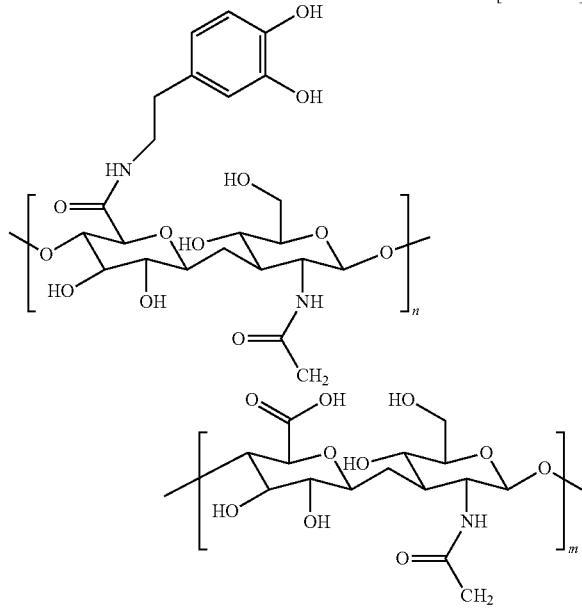

[Formula 1]

wherein the compound has a molecular weight of 35 kDa to 3 MDa, and m/(m+n) is 0.03 to 0.3, and wherein the surface modification method is carried out by immersing a reference electrode and a counter electrode in the solution to form a three electrode cell and conducting a potentiostatic method.

2. The method according to claim 1, wherein
the electrode is an ITO electrode or a gold electrode,
the reference electrode is a silver/silver chloride reference electrode, and
the counter electrode is a Pt electrode.

3. The method according to claim 2, wherein the solution has a concentration of the compound of 1 to 10 mg/mL and a pH of 2 to 7.

4. The method according to claim 3, wherein the current is applied at a constant potential within a range of 0.6 to 1.6 V for 100 to 600 seconds.

5. The method according to claim 1, wherein the compound is formed by bonding between dopamine and hyaluronic acid.

* * * * *